(12) United States Patent
O'Rourke et al.

(10) Patent No.: US 6,976,849 B2
(45) Date of Patent: Dec. 20, 2005

(54) PINLESS SOLDER JOINT FOR COUPLING CIRCUIT BOARDS

(75) Inventors: John O'Rourke, Minneapolis, MN (US); Peter J. Lamb, Minneapolis, MN (US); Bart A. Carey, Roseville, MN (US); Patrick J. Barry, North Saint Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/822,471

(22) Filed: Apr. 12, 2004

(65) Prior Publication Data

US 2005/0227506 A1     Oct. 13, 2005

(51) Int. Cl.[7] .......................... H01R 12/00; H05K 1/00
(52) U.S. Cl. ............................. 439/65; 439/69; 439/74; 174/266
(58) Field of Search ............................. 439/65, 69, 71, 439/74; 174/266, 255

(56) References Cited

U.S. PATENT DOCUMENTS

| | | | |
|---|---|---|---|
| 4,830,264 A | 5/1989 | Bitaillou et al. | |
| 6,148,900 A * | 11/2000 | Yamasaki et al. | 164/80 |
| 6,196,876 B1 * | 3/2001 | Paagman | 439/607 |
| 6,345,988 B1 * | 2/2002 | Ketcham | 439/74 |
| 6,541,712 B1 * | 4/2003 | Gately et al. | 174/266 |
| 6,547,602 B2 * | 4/2003 | Price et al. | 439/638 |
| 6,759,596 B1 * | 7/2004 | Shelnut et al. | 174/255 |
| 6,818,837 B2 * | 11/2004 | Okami | 174/260 |
| 2002/0063146 A1 | 5/2002 | Bernier et al. | |
| 2003/0070837 A1 * | 4/2003 | Okami | 174/260 |
| 2004/0092174 A1 * | 5/2004 | Eichorn et al. | 439/876 |

\* cited by examiner

Primary Examiner—Chandrika Prasad
(74) Attorney, Agent, or Firm—Faegre & Benson LLP

(57) ABSTRACT

A technique for connecting a first circuit board to a second circuit board includes aligning appropriate apertures in the circuit boards and forming a solder joint through the aligned apertures. In one application, the techniques of the present invention are used to connect circuit boards of an implantable medical device, such as a cardiac rhythm management device.

38 Claims, 8 Drawing Sheets

PINLESS SOLDER JOINT FOR COUPLING CIRCUIT BOARDS

TECHNICAL FIELD

The present invention relates to a technique for electrically coupling one circuit board to another. More specifically, the present invention relates to a technique for coupling circuit boards using a pinless solder joint.

BACKGROUND

Implantable medical devices, such as cardiac rhythm management devices (e.g., pacing systems and defibrillators) and a variety of implantable muscle or nerve stimulators, conventionally include a battery-powered electronic pulse generator coupled to an electronic circuit assembly contained within a sealed metal housing. The electronic circuit assembly typically comprises a plurality of interconnected printed circuit boards ("PCBs") that function to control the operation of the implantable device.

Ongoing efforts by the industry to reduce the size of the implantable devices have been very successful. With advances in microelectronics and integrated circuitry, significantly more features and capabilities have been embodied in implantable devices. Nonetheless, efforts to further reduce the size of implantable pulse generators continue in the industry.

Typically, PCBs are interconnected, both mechanically and electrically, with pinned joints. A circuit board has a conductive trace terminating at an aperture in the board. One end of a pin is inserted into the aperture, while the other end is inserted into the aperture of another board. The pin is then soldered to both boards to secure and improve the quality of the connection. Unfortunately, the pin protrudes from both boards, enlarging the overall dimensions of the electronic circuit assembly. Further, it can be difficult to manufacture, process, and transport the PCBs without damaging the pins.

A significant concern for manufacturers of implantable electronic tissue stimulating devices is ensuring an adequate level of quality control in the electronic circuit assembly, and in particular in the circuit board interconnections. In some applications, such as cellular phones, adequate quality control of circuit board interconnections may be ensured by random spot-checks in each batch. However, in the implantable medical device industry, quality control standards are considerably more stringent.

Often, adequate quality control of circuit board interconnections can be maintained only by checking each component individually for compliance with specifications. There is a need in the art for a PCB assembly in which each interconnection can be easily manufactured, is durable, and can be quickly and easily checked for compliance with quality control standards.

SUMMARY

The present invention, in one embodiment, is a circuit board assembly including a first circuit board having a first aperture therethrough and a second circuit board having a second aperture therethrough. The second circuit board is disposed generally parallel to the first circuit board, such that the second aperture is generally aligned with the first aperture. A solder joint extends into the first aperture and the second aperture.

The present invention, in another embodiment, is an implantable medical device including a housing, a battery located in the housing, a first circuit board having a first aperture, and a second circuit board having a second aperture. The second circuit board is disposed such that the first aperture is generally aligned with the second aperture. A solder joint extends into the first aperture and the second aperture.

The present invention, in yet another embodiment, is a method of coupling a first circuit board having a first aperture to a second circuit board having a second aperture to provide a circuit board assembly for an implantable medical device. The method includes aligning the first aperture with the second aperture, feeding an amount of solder into the first aperture, and applying heat to the first aperture for a period of time sufficient to cause the solder to flow into the second aperture.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
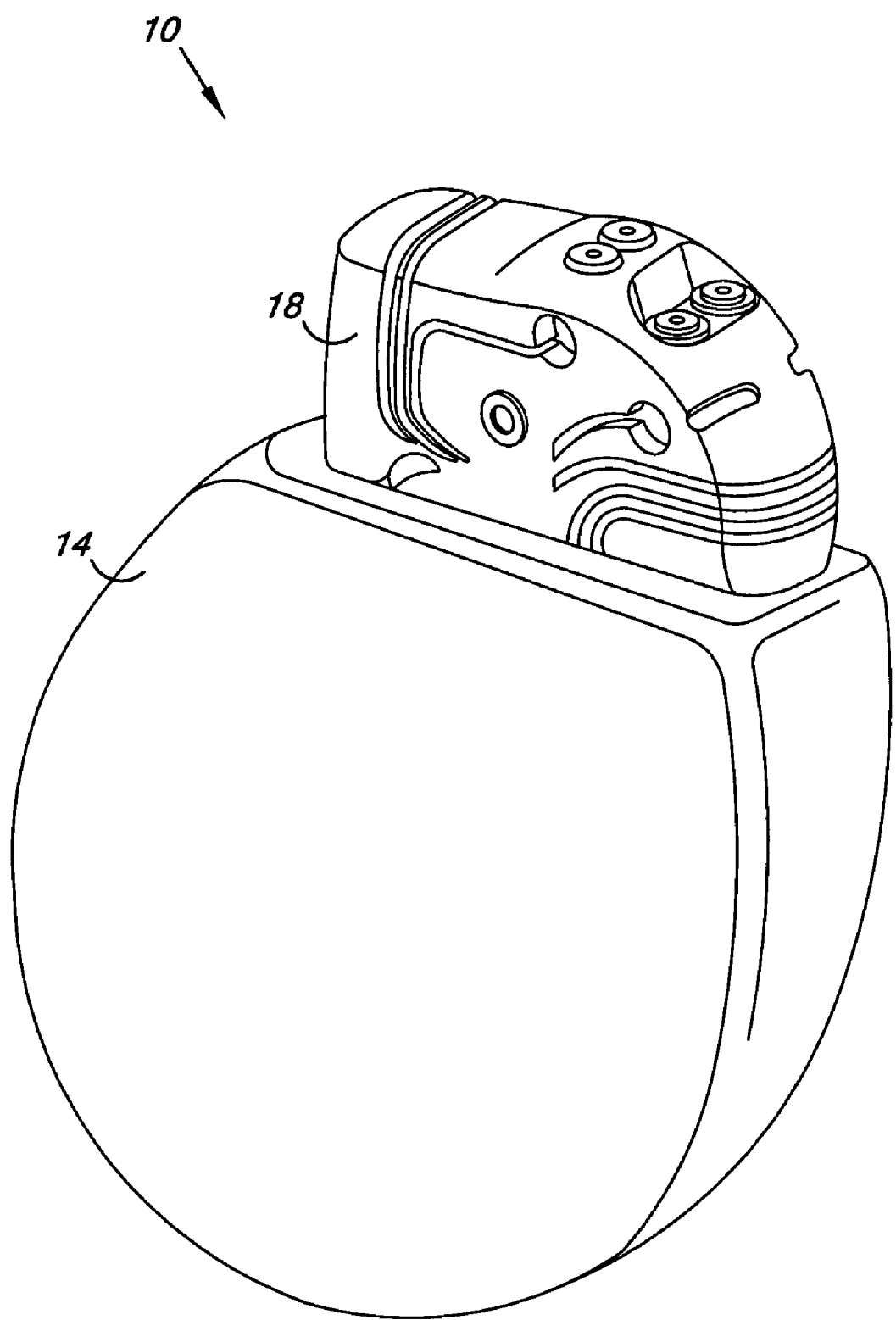
FIG. 1 is a perspective view of a cardiac pacing device according to one embodiment of the present invention.

FIG. 1 is a perspective view showing one embodiment of an implantable medical device 10 in which the present invention may be implemented. As shown in FIG. 1, the implantable device 10 includes a sealed metal housing or case 14 and an insulated top or header 18. Exemplary implantable medical devices include cardiac rhythm management devices, such as pacing systems, defibrillator/cardioverter devices, and cardiac monitors. The implantable medical device 10 is exemplary of one type of device in which the connection techniques of the present invention may be employed. The following description is presented in the context of an implantable medical device for illustrative purposes only and should not be regarded as limiting the invention. Instead, the techniques of the present invention are applicable to connecting PCBs in any setting.

Figure 2:
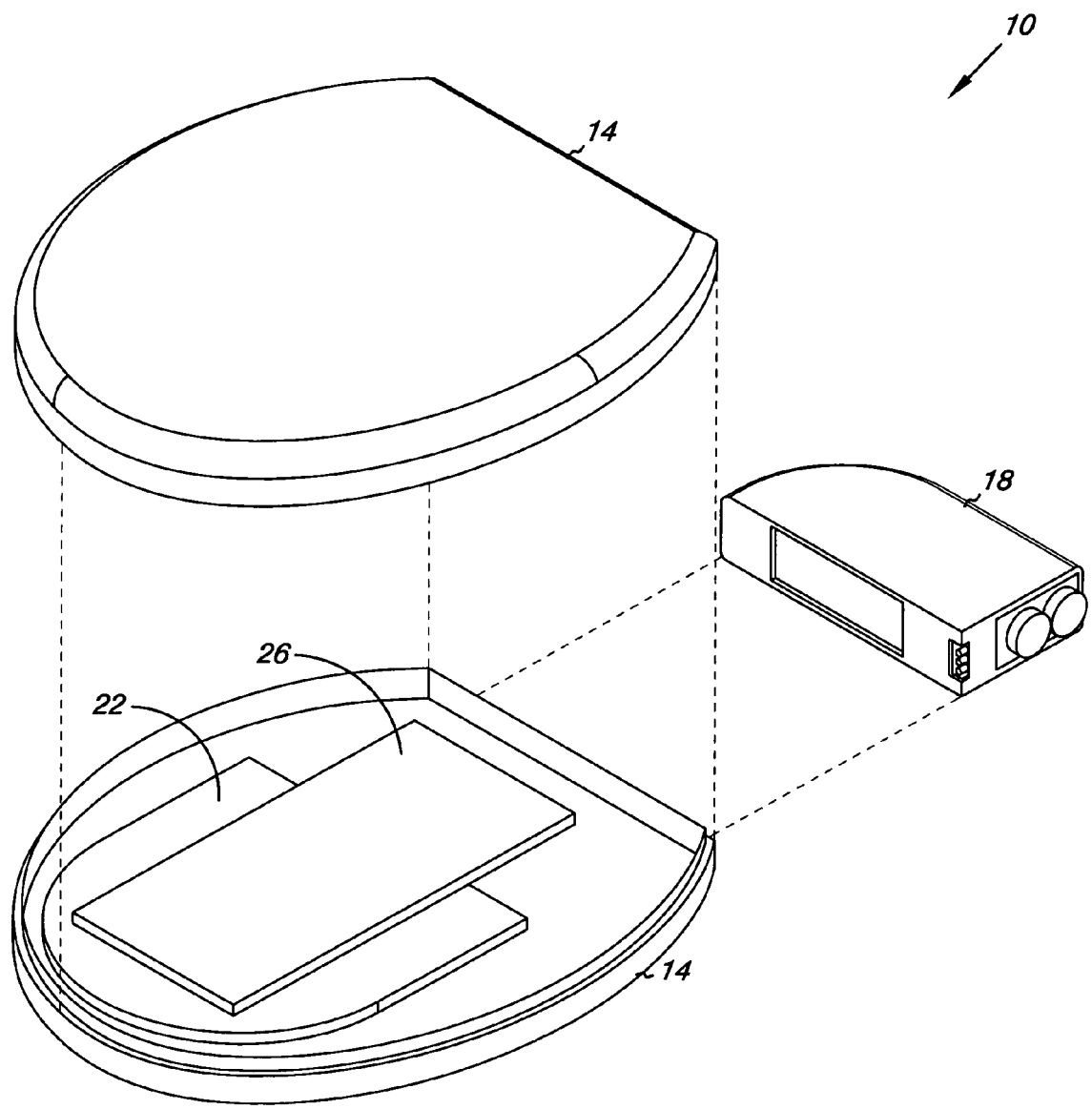
FIG. 2 is an exploded perspective view of a cardiac pacing device according to one embodiment of the present invention.

FIG. 2 is an exploded perspective view showing the interior of the implantable device 10 of FIG. 1. As shown in FIG. 2, a battery 22 and an electronic circuit assembly 26 are located inside the housing 14. The battery 22 provides power to the electronic circuit assembly 26, which controls pacing functions.

Figure 3A:
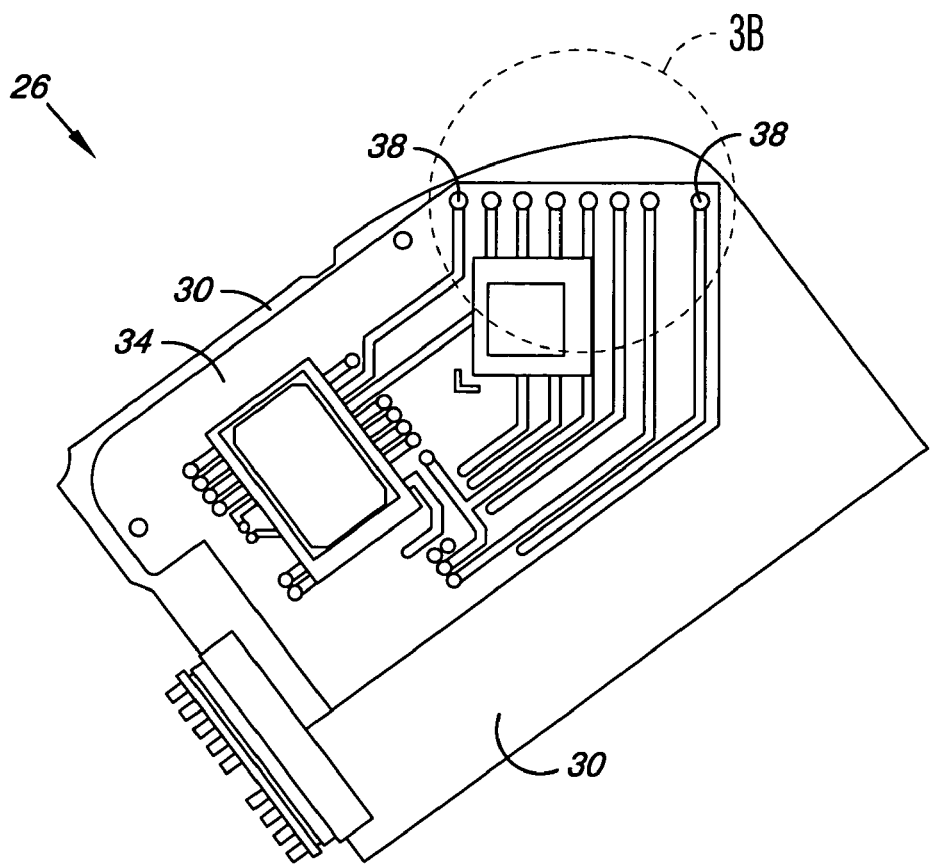
FIG. 3A is a top plan view of an electronic circuit assembly according to one embodiment of the present invention.
Figure 3B:
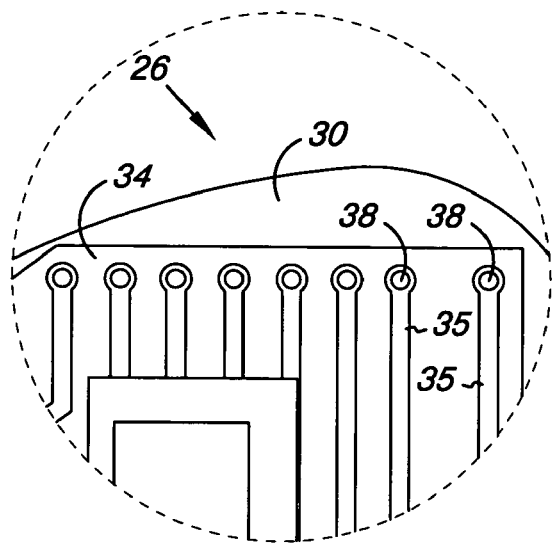
FIG. 3B is a top plan view of a portion of FIG. 3A.

FIG. 3 is a perspective view of an electronic circuit assembly 26 according to one embodiment of the present invention. As shown in FIG. 3A, the electronic circuit assembly 26 includes a first circuit board 30, which may be a mother board, coupled to a second circuit board 34, which may be a daughter board. The electronic circuit assembly 26 may include two or more interconnected circuit boards containing circuitry for performing the functions needed to control the implantable medical device 10. The first circuit board 30 is coupled to the second circuit board 34 via at least one, but possibly several, pinless solder joints 38. Where the electronic circuit assembly 26 comprises more than two circuit boards, a given circuit board may be interconnected with more than one other circuit board. According to one embodiment of the present invention, as shown in FIG. 3B, either or both of the first circuit board 30 and the second circuit board 34 are printed with at least one, but possibly several, conductive traces 35. The conductive traces 35 may be printed adjacent the joints 38, allowing the first circuit board 30 to be electrically coupled to the second circuit board 34 by the solder joints 38.

Figure 4:
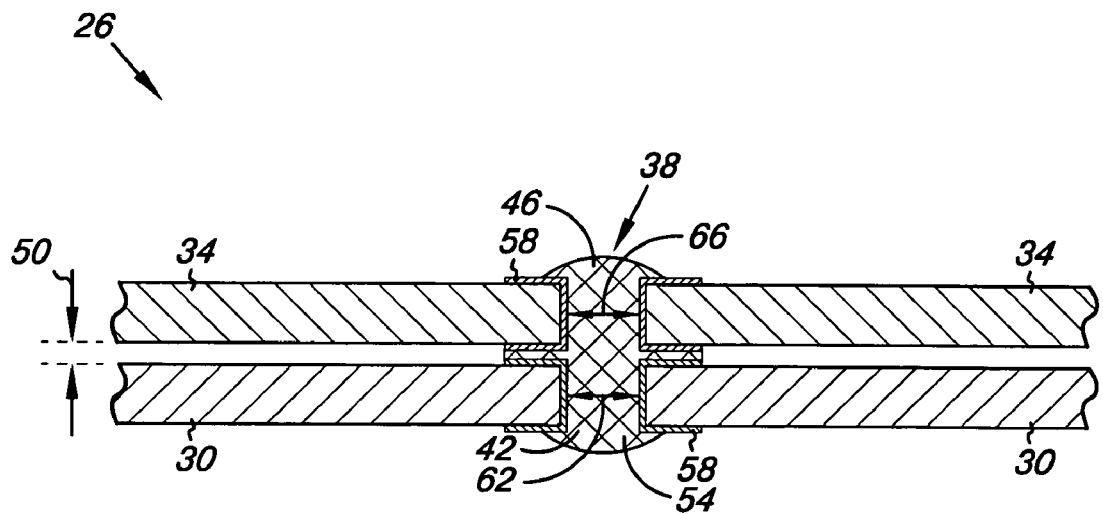
FIGS. 4–7 are partial sectional views of the electronic circuit assembly, showing the pinless solder joint according to various embodiments of the present invention.

FIG. 4 is a partial sectional view of the electronic circuit assembly 26, including a pinless solder joint 38, according to one embodiment of the present invention. As shown in FIG. 4, the first circuit board 30 has a first aperture 42, and the second circuit board 34 has a second aperture 46. In one embodiment, the apertures 42 and 46 have a generally circular shape. The first and second circuit boards 30, 34 may be printed with conductive traces 35, which may be printed adjacent the apertures 42, 46. The first circuit board 30 and the second circuit board 34 are disposed with opposed broad surfaces, such that the first aperture 42 is generally aligned with the second aperture 46. In one embodiment, in which the first circuit board 30 and the second circuit board 34 each include multiple apertures 42 and 46, the circuit boards 30, 34 are positioned such that all apertures 42, 46 requiring connection with a solder joint 38 are generally aligned. The first circuit board 30 is slightly spaced from the second circuit board 34, such that there is a gap 50 between the first circuit board 30 and the second circuit board 34.

The first circuit board 30 is coupled to the second circuit board 34 with a quantity of solder 54 at the joint 38. As shown in FIG. 4, the solder 54 substantially fills the first aperture 42, the second aperture 46 and the gap 50 adjacent the first and the second apertures 42, 46. The pinless solder joint 38 presents a low profile protruding from the first and second circuit boards 30, 34, which reduces the overall dimensions of the electronic circuit assembly 26. The joint 38 is also less likely to be damaged during other manufacturing and processing steps, as well as during transportation.

Figure 5:
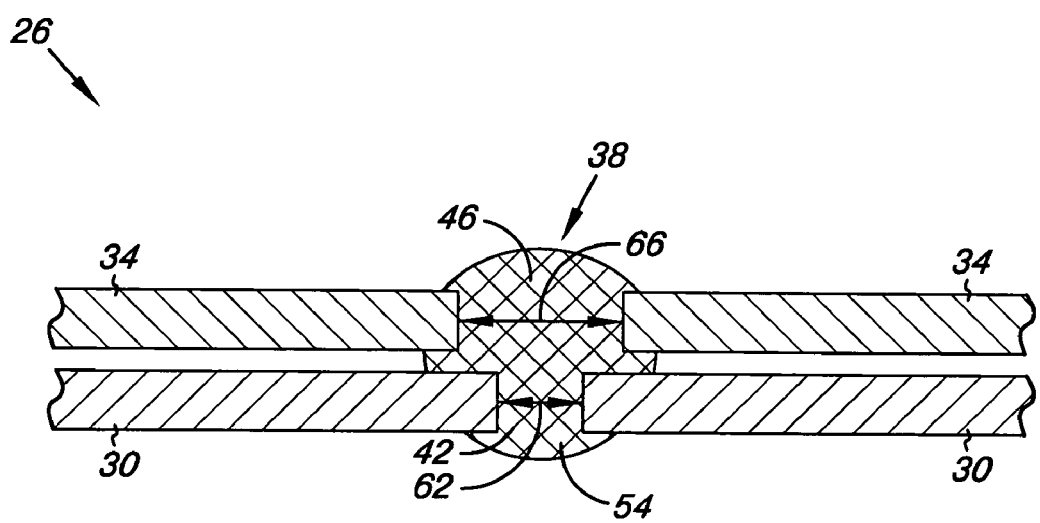

As illustrated in FIGS. 4 and 5, the first circuit board 30 is slightly spaced from the second circuit board 34 providing a gap 50. The gap 50 provides a space for any additional components on the first circuit board 30 and the second circuit board 34 that may have a raised profile. The gap 50 further provides additional surface area for the solder 54 to bond to, thereby strengthening the joint 38. The dimensions of the gap 50 may be decreased to reduce the overall profile of the electronic circuit assembly 26. Alternately, the dimensions of the gap 50 may be increased to allow a greater volume of the solder 54 to locate at the solder joint 38, thus increasing the joint strength. According to one embodiment of the present invention, gap 50 is generally from about 0 to 0.01 inches. According to another embodiment of the present invention, the gap 50 is generally from about 0.001 to about 0.006 inches. According to yet another embodiment of the present invention, the gap 50 is generally about 0.002 inches.

Figure 6:
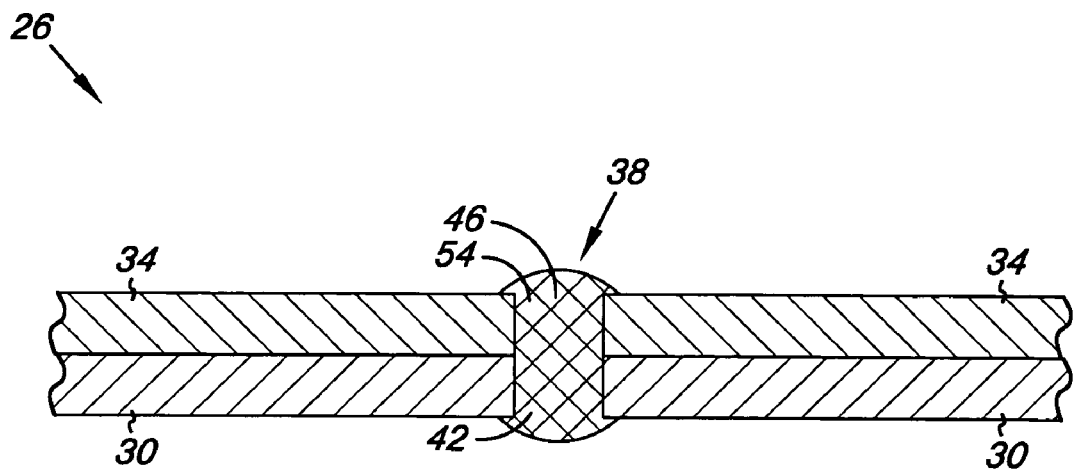

According to another embodiment of the present invention, as shown in FIG. 6, the first circuit board 30 is adjacent the second circuit board 34, such that the gap 50 is substantially eliminated. Eliminating the gap 50 reduces the overall profile of the electronic circuit assembly 26. However, eliminating the gap 50 also reduces the amount of surface area available for the solder 54 to bond to, which may reduce the strength of the joint 38. According to another embodiment of the present invention, the gap 50 is not generally equal across the opposed broad surfaces of the first circuit board 30 and the second circuit board 34.

As shown in FIG. 4, according to one embodiment of the present invention, the first aperture 42 and the second aperture 46 are coated with a layer of copper 58 under the solder 54. The copper layer 58 may electrically couple the printed conductive traces 35 to the first and the second apertures 42, 46. As the solder 54 is typically electrically conductive, the first circuit board 30 and the second circuit board 34 may be electrically, as well as mechanically, coupled to one another via the joint 38. In one embodiment, the copper layer 58 is printed on one surface of the circuit boards 30, 34. In another embodiment, the copper layer 58 is printed on both surfaces of the circuit boards 30, 34.

The first aperture 42 has a first diameter 62 and the second aperture 46 has a second diameter 66. According to one exemplary embodiment of the present invention, as shown in FIG. 4, the first diameter 62 is generally equal to the second diameter 66. According to another embodiment, the first diameter 62 and the second diameter 66 are from about 0.01 to about 0.04 inches. According to yet another embodiment, the first diameter 62 and the second diameter 66 are from about 0.015 to about 0.022 inches. The diameters may also be of any other size typical in printed circuit boards. According to another embodiment of the present invention, as shown in FIG. 5, the first diameter 62 is different than the second diameter 66. In one embodiment, the first diameter 62 is from about 70 to about 130 percent of the second diameter 66. In another embodiment, the first diameter 62 is from about 90 to about 110 percent of the second diameter 66.

Figure 7:
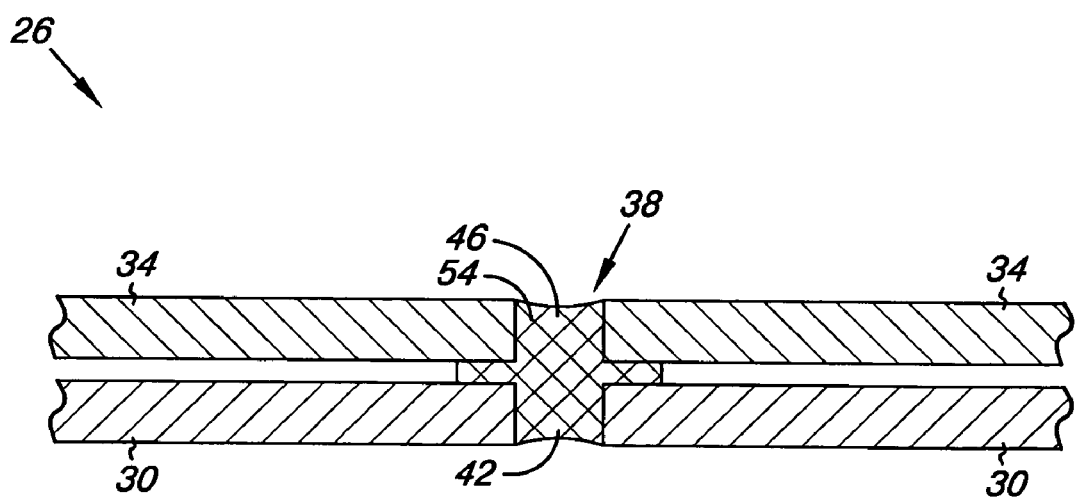

As shown in FIGS. 4–6, the joint 38 includes an amount of solder 54 sufficient to fill and extend outwardly from the apertures 42 and 46. In one embodiment, the curvature of the solder joint 38 is dictated by the surface tension of the solder 54. According to another embodiment, as shown in FIG. 7, the solder 54 fails to completely fill the apertures 42 and 46. In another embodiment, the solder 54 fills the apertures 42, 46 such that the solder 54 is generally level with the surface of the circuit boards 30, 34.

According to one embodiment of the present invention, the solder 54 includes flux. The solder-flux composition leaves a reduced amount of ionic residues at the completion of the soldering process. Known as "no-clean" solder, the solder-flux composition of the present invention substantially reduces the amount of cleaning needed to remove ionic residues following the soldering process. The solder-flux composition may be provided by a solder wire having flux. In one embodiment, the solder 54 is comprised of from about 1 to about 10 percent flux by weight. In another embodiment, the solder 54 is comprised of about 2 percent flux by weight. In one embodiment, the solder 54 does not contain flux. Instead, flux may be provided separately.

Figure 8A:
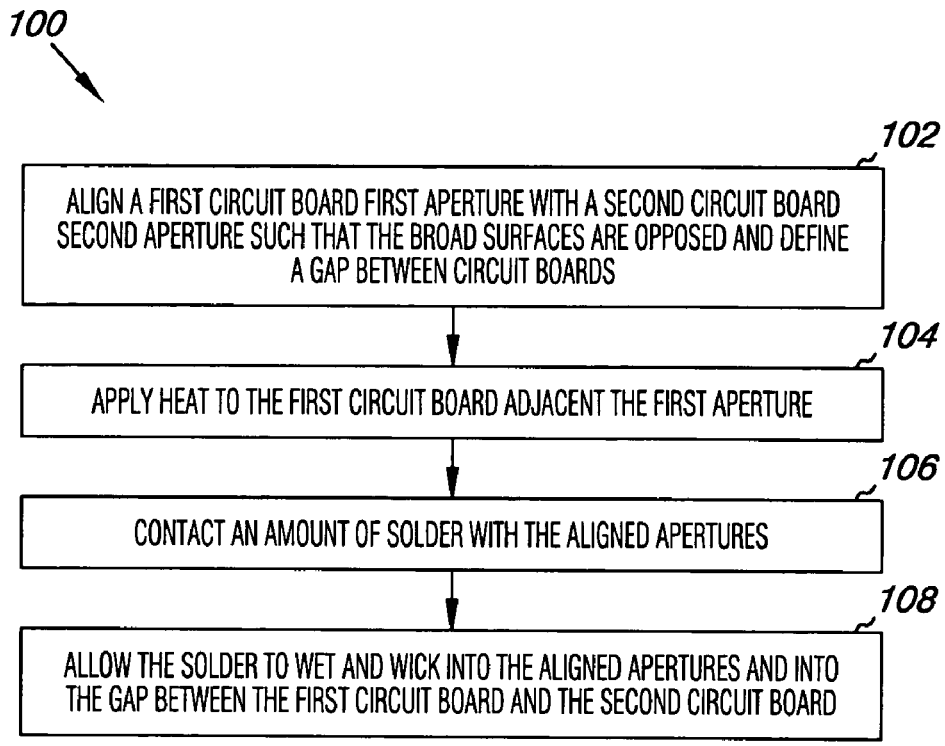
FIG. 8A is a flow chart showing a method for providing a pinless solder joint according to one embodiment of the present invention.

FIG. 8A is a flowchart depicting one embodiment of a method 100 for providing a pinless solder joint. First, one or more apertures of a first circuit board are aligned with one or more apertures of a second circuit board, such that the broad surfaces are generally opposed and define a gap between the circuit boards (block 102). Then, heat is applied to the first circuit board adjacent the first aperture for a period of time sufficient to raise the temperature of the board to a level sufficient to allow solder to melt and flow (block 104). Next, an amount of solder is contacted with the aligned apertures (block 106). Finally, the solder flows into the aligned apertures and into the gap between the first circuit board and the second circuit board (block 108).

Figure 8B:
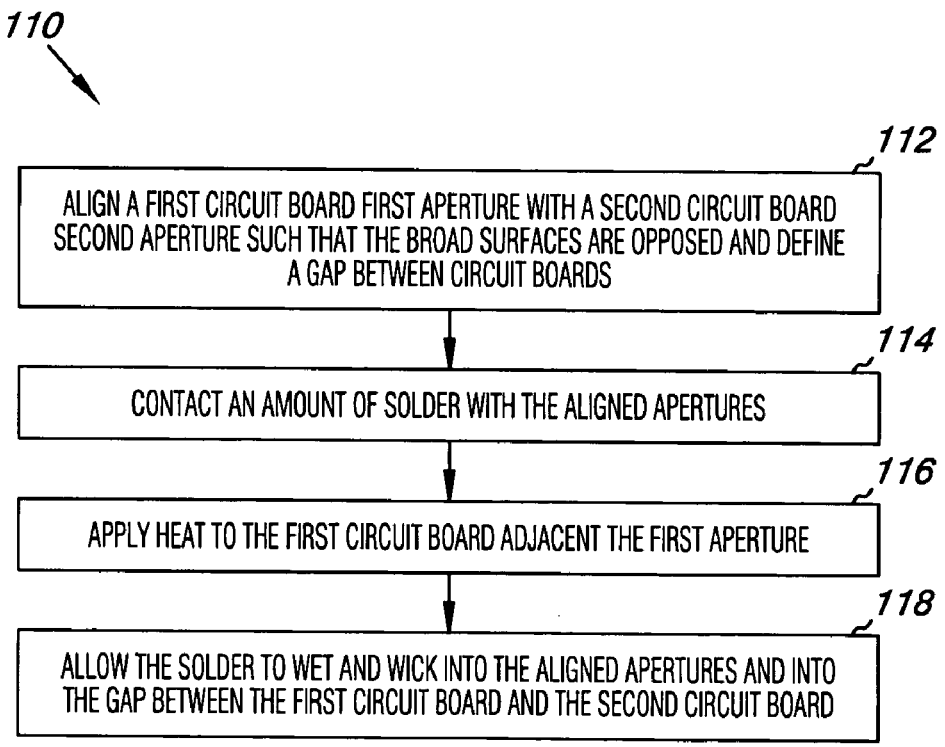
FIG. 8B is a flow chart showing a method for providing a pinless solder joint according to another embodiment of the present invention.

FIG. 8B is a flowchart depicting another embodiment of a method 110 for providing a pinless solder joint. First, one of more apertures of a first circuit board are aligned with one or more apertures of a second circuit board, such that the broad surfaces are opposed and define a gap between the circuit boards (block 112). Next, an amount of solder is contacted with the aligned apertures (block 114). Then, heat is applied to the first circuit board adjacent the first aperture for a period of time sufficient to raise the temperature of the board to a level sufficient to allow solder to melt and flow (block 116). Finally, the solder flows into the aligned apertures and into the gap between the first circuit board and the second circuit board (block 118).

Figure 9A:
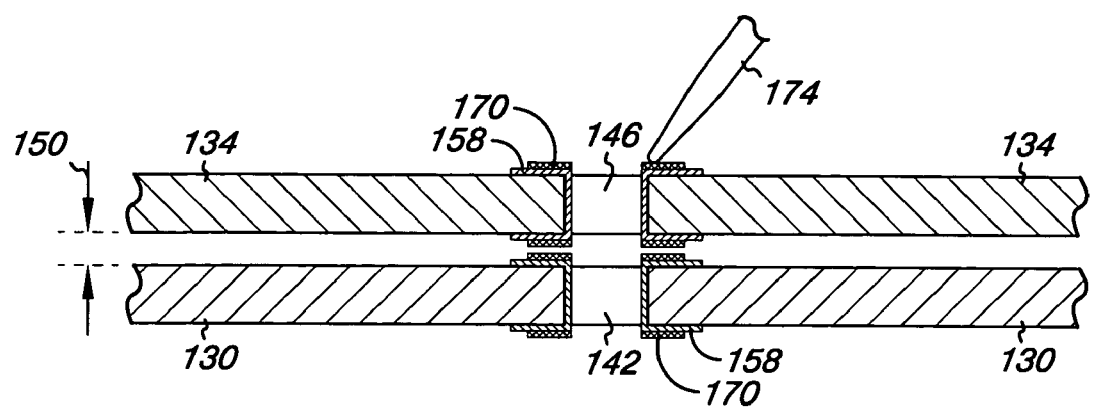
FIGS. 9A–9C are partial sectional views showing stages in manufacturing a pinless solder joint according to one embodiment of the present invention.
Figure 9B:
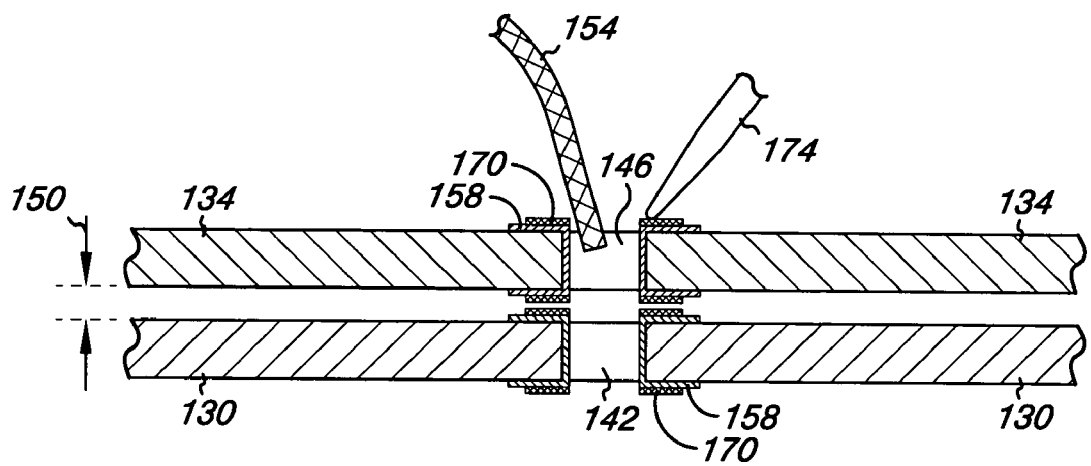
Figure 9C:
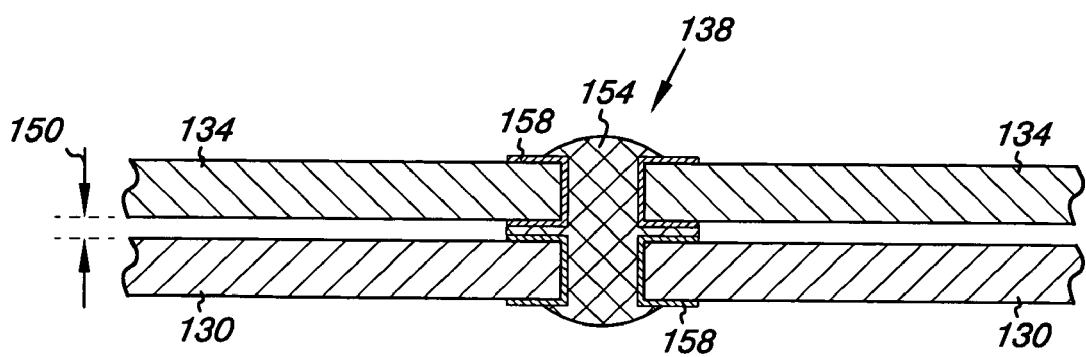

FIGS. 9A–9C illustrate various stages of a method for providing a pinless solder joint 138 according to one embodiment of the present invention. As shown in FIG. 9A, a first circuit board 130 and a second circuit board 134 are placed in a spaced relationship, one atop the other with a gap 150 therebetween. The first circuit board 130 has a first aperture 142 and the second circuit board 134 has a second aperture 146. The first aperture 142 and the second aperture 146 generally are aligned with one another. A copper coating 158 is provided around the first aperture 142 and second aperture 146. According to one embodiment, the first and second circuit boards 130 and 134 are further provided with a layer of pre-printed solder 170 around the first and second apertures 142 and 146. The pre-printed solder 170 is printed over the copper coating 158. According to another embodiment, a layer of solder is pre-printed over the first and second apertures 142 and 146 (not shown). The addition of pre-printed solder 170 may help to prevent voids forming in the subsequent solder joint.

A heat source, for example a soldering iron 174, is applied to the second circuit board 134 so as to provide heat to melt, or wet, the preprinted solder 170 and subsequently added solder 154. In other embodiments, the heat source 174 is a hot plate, an infrared heat source, or a reflow oven. The heat source 174 is generally about the same temperature as the melting point of the preprinted solder 170 and the solder 154. Solder is typically available having a range of melting points. According to one embodiment, the heat source 174 is generally about 183° C. According to another embodiment, the heat source is generally about 179° C. In order to protect other components in the electrical circuit assembly, it may be desirable to employ solder having a lower melting point so that less heat need be applied to melt the solder.

The heat source 174 is applied for a period of time sufficient to cause the solder 154 to melt. This amount of time varies and is influenced by several factors. First, both the first circuit board 130 and the second circuit board 134 function as heat sinks and must be heated sufficiently to allow the solder 154 to melt. The thicker the first circuit board and the second circuit board are, the longer the heat source 174 must be applied to provide sufficient heat to melt the solder 154. Second, as discussed above, the apertures 142, 146 may be coated with a layer of copper 158 underneath any pre-printed solder 170. The copper coating 158 functions as a heat sink as well. Therefore, the more copper 158 that is applied the longer the heat source 174 must be applied to provide sufficient heat to melt the solder 154. In one embodiment, the heat source 174 is applied from about 2 to about 6 seconds. In another embodiment the heat source 174 is applied for about 4 seconds.

After sufficient heat is provided, as shown in FIG. 9B, the solder 154 is contacted with the second aperture 142. The solder 154 melts or wets, allowing the solder 154 to flow into the second aperture 146. Additional solder 154 is fed into the second aperture 146, causing the solder 154 to flow into the gap 150 and into and through the first aperture 142. The heat source 174 is removed, which allows the solder 154 to cool and harden, shown in FIG. 9C, coupling the first circuit board 130 to the second circuit board 134. Alternately, the heat 174 may be applied to first circuit board 130. Once the solder 154 has hardened, the solder joint 138 may be visually inspected from both the first circuit board side and the second circuit board side.

According to another embodiment of the present invention the solder 154 is contacted adjacent the second aperture 146, or placed partially within the aperture 146, before heat is applied. The heat 174 is then applied to the second circuit board 134 adjacent the second aperture 146 for a period of time sufficient to cause the solder 154 to melt or wet. As before, the solder 154 flows through the second aperture 146 and wicks into the gap 150 and into and through the first aperture 142.

Surface tension in the wetted solder 154 produces a naturally curved profile at the first and second apertures 142, 146 when the solder 154 hardens. During manufacture, the first circuit board 130 (or whichever circuit board is on the bottom) may be placed on a flat surface to provide support and stability during the soldering process. In one embodiment, the support surface has a slightly concave profile, or at least a portion of the surface has a concave profile. The first aperture 142 may be placed over the concave portion so that the support surface does not interfere with or prevent the formation of a curved profile.

Figure 10A:
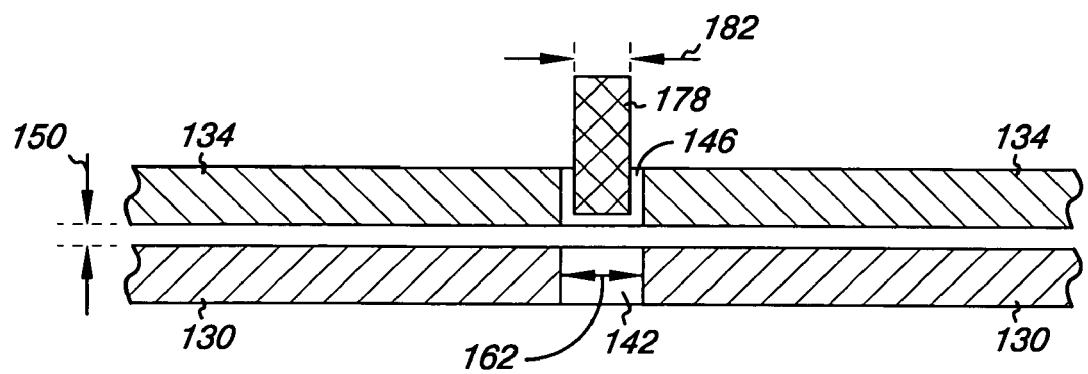
FIGS. 10A–10C are partial cross-sectional views showing stages in manufacturing a pinless solder joint according to yet another embodiment of the present invention.
Figure 10B:
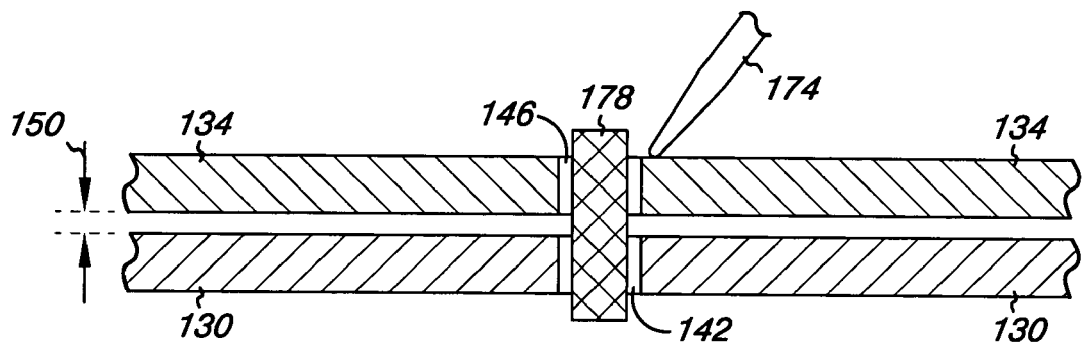
Figure 10C:
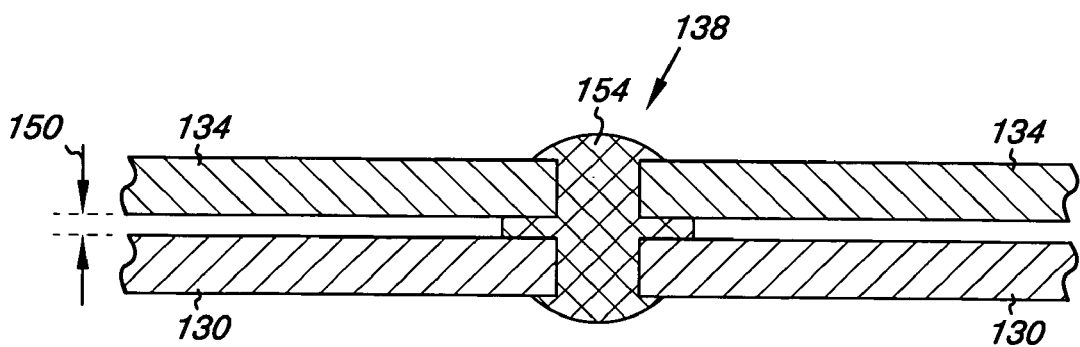

FIGS. 10A–10C illustrate another method for producing a pinless solder joint. As shown in FIG. 10A, a solder core 178 is positioned in the open space defined by the apertures 142 and 146. The solder core 178 may include flux. In one embodiment, the solder core 178 has a flux composition of from about 1 to about 10 percent by weight. In another embodiment, the solder core 178 has a flux composition of about 2 percent. According to one embodiment, the solder core 178 may be preformed having a defined length. The length may be selected to provide a sufficient quantity of solder to form a proper joint. In this manner, especially during automated processes, variations in the quantity of solder applied to each joint are reduced. According to one embodiment, the solder core 178 has a length equal to the thickness of the first circuit board 130, the second circuit board 134, and the gap 150 between the first circuit board 130 and the second circuit board 134. According to another embodiment, the solder core 178 has a length greater than the thickness of the first circuit board 130, the second circuit board 134, and the gap 150 between the first circuit board 130 and the second circuit board 134.

In one embodiment, the solder core 178 has a diameter 182 only slightly smaller than the first aperture diameter 162 or the second aperture diameter 166. Using the largest diameter solder core 178 that will fit into the space created by the first aperture 142 and the second aperture 146 reduces the amount of time need to produce the joint. Using larger diameter solder may also decrease the incidence of voids occurring in the solder joint. According to one embodiment, the solder core diameter 182 is generally from about 0.01 to about 0.04 inches. According to another embodiment, the solder core diameter 182 is generally from about 0.015 to about 0.025 inches. According to another embodiment, the solder core 178 has a greater diameter at a generally central region (not shown).

According to FIG. 10B, a heat source, for example a soldering iron 174, is applied to the second circuit board 134. In other embodiments, the heat source 174 is a hot plate, an infrared heat source, or a reflow oven. The heat source 174 is applied for a period of time sufficient to cause the solder core 178 to melt. In one embodiment, the heat source 174 is applied for an amount of time from about 2 to about 6 seconds. In another embodiment, the heat source 174 is applied for about 4 seconds.

The heat source 174 wets or melts the solder core 178, allowing the solder 178 to flow into the second aperture 146. The heat 174 is removed, which allows the solder 178 to cool and harden, shown in FIG. 10C, coupling the first circuit board 130 to the second circuit board 134 at a solder joint 138. Alternately, the heat source 174 may be applied to first circuit board 130 or both circuit boards 130, 134 simultaneously. Once the solder 178 has hardened, the solder joint 138 may be visually inspected from both the first circuit board side and the second circuit board side.

Although the present invention has been described with reference to exemplary embodiments, persons skilled in the art will recognize that changes may be made in form and detail without departing from the spirit and scope of the invention.

We claim:

1. A circuit board assembly comprising:
   a first circuit board having a first aperture therethrough;
   a second circuit board having a second aperture therethrough, the second circuit board disposed generally parallel to the first circuit board such that the second aperture is generally aligned with the first aperture and such that there is an air gap between the first and second circuit boards; and
   a solder joint extending into the first aperture and the second aperture and substantially filling the gap between the first and the second apertures, the solder joint electrically and mechanically coupling the first circuit board to the second board, and wherein a portion of the solder joint is visible from the first circuit board and the second circuit board.

2. The circuit board assembly of claim 1 wherein the first aperture has a first diameter and the second aperture has a second diameter.

3. The circuit board assembly of claim 2 wherein the first diameter and the second diameter are greater than about 0.01 inches and less than about 0.04 inches.

4. The circuit board assembly of claim 2 wherein the first diameter and the second diameter are substantially equal to 0.022 inches.

5. The circuit board assembly of claim 2 wherein the first diameter is different from the second diameter.

6. The circuit board assembly of claim 5 wherein the ratio of the first diameter to the second diameter is greater than 70 percent and less than 130 percent.

7. The circuit board assembly of claim 5 wherein the ratio of the first diameter to the second diameter is greater than about 90 percent and less than about 110 percent.

8. The circuit board assembly of claim 1 wherein the gap is less than about 0.006 inches at or near the solder joint.

9. The circuit board assembly of claim 1 wherein the gap is substantially equal to 0.002 inches at or near the solder joint.

10. The circuit board assembly of claim 1 further including a copper layer coating the first aperture and the second aperture.

11. The circuit board assembly of claim 1 wherein the solder joint is comprised of a combination of solder and flux.

12. The circuit board assembly of claim 11 wherein the solder is comprised of greater than about 1 and less than about 10 percent flux by weight.

13. The circuit board assembly of claim 11 wherein the solder is comprised of about 2 percent flux by weight.

14. The circuit board assembly of claim 1 wherein either or both of the first circuit board and the second circuit board are printed with conductive traces.

15. The circuit board assembly of claim 14 wherein the conductive traces of the first circuit board are electrically coupled to the conductive traces of the second circuit board by the solder joint.

16. An implantable medical device comprising a housing, a battery located in the housing, a first circuit board having a first aperture, a second circuit board having a second aperture, the second circuit board disposed such that the first aperture is generally aligned with the second aperture and such that there is an air gap between the first and second circuit boards, and a solder joint extending into the first aperture and the second aperture and electrically and mechanically coupling the first circuit board to the second circuit board, wherein the solder joint substantially fills the gap between the first and second apertures and a portion of the solder joint is visible from the first circuit board and the second circuit board.

17. The implantable medical device of claim 16 wherein the device is a cardiac rhythm management device.

18. The implantable medical device of claim 17 wherein the first aperture has a first diameter and the second aperture has a second diameter.

19. The implantable medical device of claim 18 wherein the first diameter is equal to the second diameter.

20. The implantable medical device of claim 19 wherein the first diameter and the second diameter are substantially equal.

21. The implantable medical device of claim 19 wherein the first diameter and the second diameter are greater than about 0.01 inches and less than about 0.04 inches.

22. The implantable medical device of claim 18 wherein the first diameter is different from the second diameter.

23. The implantable medical device of claim 22 wherein the ratio of the first diameter to the second diameter is greater than about 70 percent and less than about 130 percent.

24. The implantable medical device of claim 22 wherein the ratio of the first diameter to the second diameter is greater than about 90 percent and less than about 110 percent.

25. The implantable medical device of claim 16 wherein the gap is less than about 0.006 inches at or near the solder joint.

26. The implantable medical device of claim 16 wherein the gap is substantially equal to 0.002 inches at or near the solder joint.

27. The implantable medical device of claim 17 further including a copper layer coating the first aperture and the second aperture.

28. The implantable medical device of claim 17 wherein the solder joint is comprised of a combination of solder and flux.

29. The implantable medical device of claim 28 wherein the solder is comprised of greater than about 1 percent and less than about 10 percent flux by weight.

30. The implantable medical device of claim 28 wherein the solder is comprised of approximately 2 percent flux by weight.

31. The implantable medical device of claim 17 wherein either or both of the first circuit board and the second circuit board are printed with conductive traces.

32. The implantable medical device circuit board assembly of claim 31 wherein the conductive traces of the first circuit board are electrically coupled to the conductive traces of the second circuit board at the solder joint.

33. A method of coupling a first circuit board having a first aperture to a second circuit board having a second aperture to provide a circuit board assembly for an implantable medical device, the method comprising:

aligning the first aperture with the second aperture such that the first and second apertures are separated by an air gap therebetween;

providing an amount of solder at the first aperture;

applying heat at the first aperture for a period of time sufficient to cause the solder to flow into the gap and the second aperture; and flowing a sufficient amount of solder into the first aperture to substantially the fill the gap and the second aperture so that solder is visible at the first and second apertures.

34. The method of claim 33 wherein heat is applied for a period of time up to 4 seconds.

35. The method of claim 33 further comprising:

allowing the solder to harden; and visually inspecting the solder at the first aperture and at the second aperture.

36. The method of claim 33 wherein the amount of solder is a solder core and further wherein the solder core is provided at least partially within the first aperture prior to the step of applying heat.

37. The method of claim 33 wherein the applying step is performed before the step of providing solder.

38. The method of claim 33 wherein the first circuit board and the second circuit board are provided with a layer of solder adjacent the first aperture and the second aperture.

* * * * *

UNITED STATES PATENT AND TRADEMARK OFFICE
CERTIFICATE OF CORRECTION

| | | |
|---|---|---|
| PATENT NO. | : 6,976,849 B2 | Page 1 of 1 |
| APPLICATION NO. | : 10/822471 | |
| DATED | : December 20, 2005 | |
| INVENTOR(S) | : John O'Rourke et al. | |

It is certified that error appears in the above-identified patent and that said Letters Patent is hereby corrected as shown below:

<u>Column 9</u>

Lines 19-20, delete the words "circuit board assembly"

Signed and Sealed this

Twelfth Day of September, 2006

JON W. DUDAS
*Director of the United States Patent and Trademark Office*